United States Patent [19]

Lazzara et al.

[11] Patent Number: 5,244,390

[45] Date of Patent: Sep. 14, 1993

[54] DENTAL SCALING INSTRUMENT

[75] Inventors: Richard J. Lazzara, Lake Worth; Keith D. Beaty, West Palm Beach; Anita H. Daniels, Jupiter, all of Fla.

[73] Assignee: Implant Innovations, Inc., West Palm Beach, Fla.

[21] Appl. No.: 820,339

[22] Filed: Jan. 14, 1992

[51] Int. Cl.$^5$ .............................................. A61C 17/00
[52] U.S. Cl. .................................................. 433/143
[58] Field of Search ......................... 433/141, 143, 142

[56] References Cited

U.S. PATENT DOCUMENTS

| | | | |
|---|---|---|---|
| 1,220,933 | 3/1917 | Bates | 433/143 |
| 3,660,902 | 5/1972 | Axelsson | 433/142 |
| 4,505,678 | 3/1985 | Anderson | 433/143 |
| 4,522,595 | 6/1985 | Selvidge | 433/142 |
| 4,795,344 | 1/1989 | Brewer | 433/143 |

FOREIGN PATENT DOCUMENTS 2620328  3/1989  France ................................ 433/143

Primary Examiner—John J. Wilson
Attorney, Agent, or Firm—Alfred H. Rosen

[57] ABSTRACT

A dental scaler particularly for scaling artificial dental abutments made of a material that is softer than natural dentition, such as titanium and its dilute alloys, without scratching the surface of the abutment. Two embodiments of the scaler are disclosed; in one the scaler tip has a contact surface that is softer than the abutment surface; in the other the contact surface has a contact edge that is rounded to avoid scratching the abutment surface.

47 Claims, 3 Drawing Sheets

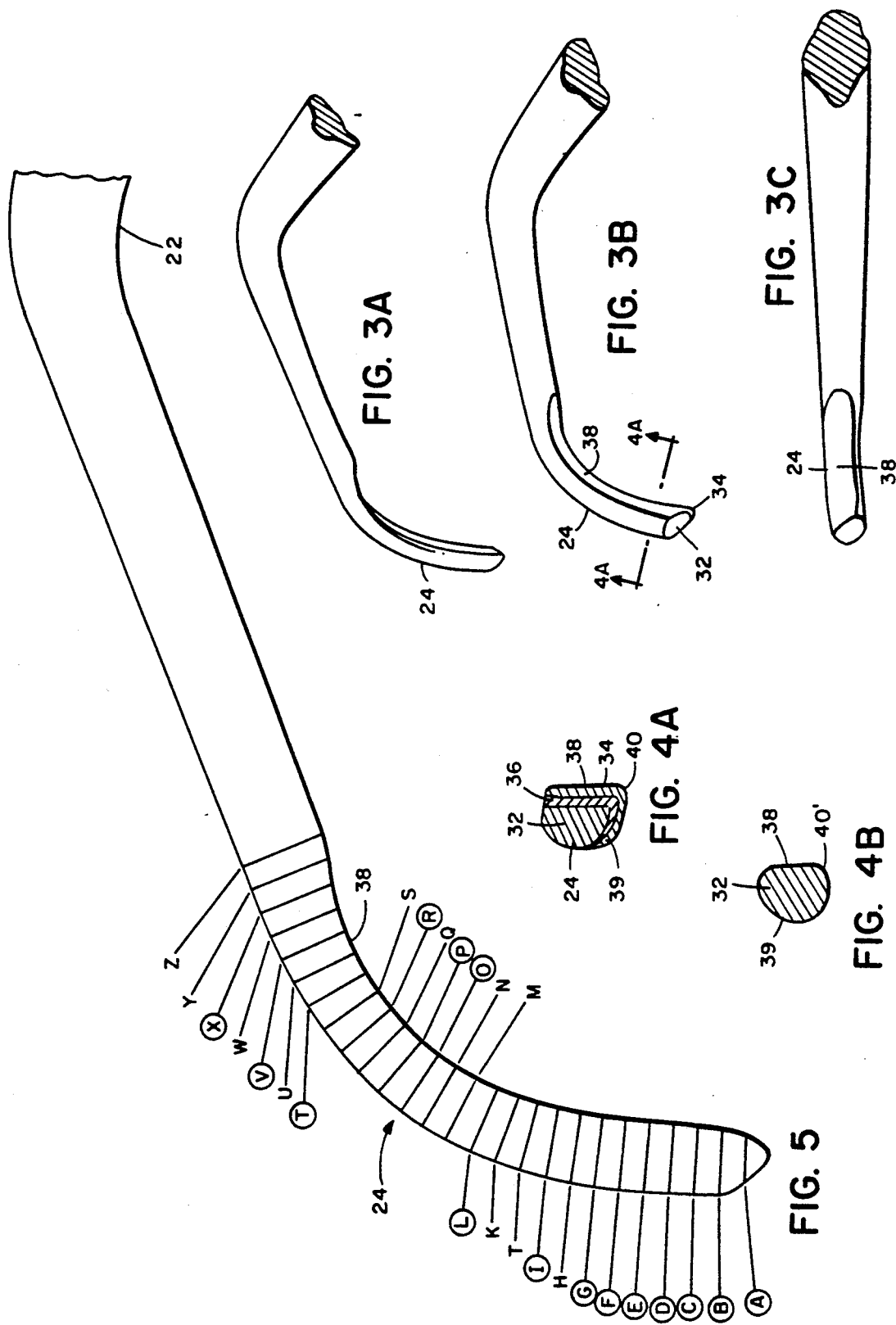

DENTAL SCALING INSTRUMENT

BACKGROUND OF THE INVENTION

This invention relates to dental scaling instruments, or curettes, more particularly to dental scalers which are uniquely useful to remove food debris and plaque from the transmucosal region of implant abutments made of relatively soft materials such as titanium and alloys of titanium or gold that are in use to support dental restorations on dental implant fixtures.

Dental scaling instruments are used to remove food debris, plaque and calculus from natural teeth in the vicinity of the gum line as well as above and below the gum line. Scaling is the scraping motion applied to a hard surface to remove debris. Instruments used to perform this operation on natural teeth are made of materials which are hard and rigid enough to remove calculus and plaque from the surfaces of natural tooth enamel and the tooth root (cementum) and flexible enough to maintain contact with those surfaces while being manipulated by the clinician or dental hygienist. In the present state of the art of dentistry stainless steel in the form of a flexible hook-like extension from a rigid handle is used to fashion dental scaling instruments. Various hook configurations and shapes are in use, among them being, but not limited to, the "universal" and the "Gracey" shapes. Hard materials like stainless steel in the currently available shapes are suitable to scale away plaque and calculus from the natural dentition without scratching or damaging the natural enamel. Natural tooth enamel is harder than stainless steel and has a smoother surface. These characteristics prevent hard materials such as stainless steel from abrading the enamel. The natural root surface however is softer (cementum) and scaling of roots is purposely done to smooth this surface.

Modern dentistry includes the new technique of implantology. In this new technique a dental implant fixture is placed in the jawbone of a patient in a location where the patient is edentulous, and an artificial tooth is supported on that implant fixture. To achieve this support a component, commonly called an abutment, which extends from the implant fixture in bone through the patient's gum, is used to unite the tooth or crown to the fixture. The portion of the abutment which exits the gum is subject to the same rigors as a natural tooth at the gum line; that is, it, too, is exposed to calculus and plaque, and a program of dental hygiene is imperative to maintain the health of the gums and the jawbone where the implant fixture is installed. In fact, such a hygiene program may be more necessary to the maintenance of an implant-supported dental restoration than for the maintenance of healthy natural teeth for the reason that if plaque and calculus are permitted to collect on the abutment and under the surface of the surrounding gingiva, bacteria will eventually attack the bone surrounding or in contact with the implant fixture, and the union between the implant fixture and the bone will eventually fail.

Titanium and its dilute alloy TiA16-4V are at the present time the materials of choice for fabrication of dental implant fixture and the components used with them, including abutments. Titanium is relatively soft compared with natural tooth enamel. The hard materials (e.g. stainless steel) presently used to make dental scaling instruments are found to scratch titanium and its dilute alloy, providing sites for bacteria to take residence and proliferate. Scratched and roughened surfaces will collect even more plaque and calculus than a smooth surface. Existing dental scaling instruments are therefore not useful to maintain dental restorations supported on dental implant fixtures. A need exists for a dental scaling instrument that can be used in a program of maintenance hygiene for a dental-implant supported restoration.

Dental scaling instruments for this purpose have been proposed using plastics materials in place of the stainless steel that is now in use, but the plastics materials that have been tried have not been satisfactory for a variety of reasons. If made thin enough to fit between and around the teeth and their supporting abutments and the gums they have been found to be too flexible to remove harder calculus deposits, or so rigid a plastic that they are brittle and break in use. If made thick enough to have adequate flexibility and strength they are too thick to fit between and around the teeth and abutments and gums being treated. Dental scaling instruments coated with titanium and titanium nitride have also been proposed, and these have been shown to scratch titanium. There is a continuing need for a dental scaling instrument useful in a program of hygiene for dental restorations supported on dental implant fixture which will have enough rigidity to remove calculus as well as plaque, will be fine enough in design to allow subgingival scaling, and will be soft enough not to scratch or abrade titanium or other abutment material. The present invention provides such instruments.

GENERAL NATURE OF THE INVENTION

According to the invention in one of its embodiments, a dental scaling instrument for use to remove plaque and calculus from abutments made of titanium and dilute titanium alloys has a scaling tip comprised of a support core and covering at least a portion of the core a contact layer made of a material that is softer than titanium for making contact with the titanium during use of the scaler. In a presently preferred version of this embodiment of the invention the core can be made of brass and the contact layer can be made of gold. Each of these components is itself softer than the abutment material. The use of gold as the contact material is preferred because of its biocompatibility. It is an example of a precious metal long used for other purposes in dentistry owing to its resistance to corrosion. Other precious metals that are softer than the abutment material may also be used as the contact material; platinum is an example. Some plastic materials may also be used as the contact material if they can be made sufficiently durable to provide a practically useful scaling instrument.

In another embodiment the invention provides a scaling tip with a rounded scaling edge to prevent the scaling tool from scratching titanium and dilute alloy titanium abutments. In that embodiment materials that are as hard as or somewhat harder than titanium may be used to provide the scaling edge.

BRIEF DESCRIPTION OF THE DRAWINGS

FIGS. 3 A, B and C are enlarged views of the scaling tip portion of FIG. 2;

FIG. 4A is a cross-section in line 4A—4A of FIG. 3B;

FIG. 4B is a cross-section illustrating another embodiment of the invention;

FIG. 5 shows cross-section lines on a scaling tip embodying the invention of FIG. 4B.

DETAILED DESCRIPTION OF THE DRAWINGS

Figure 1A:
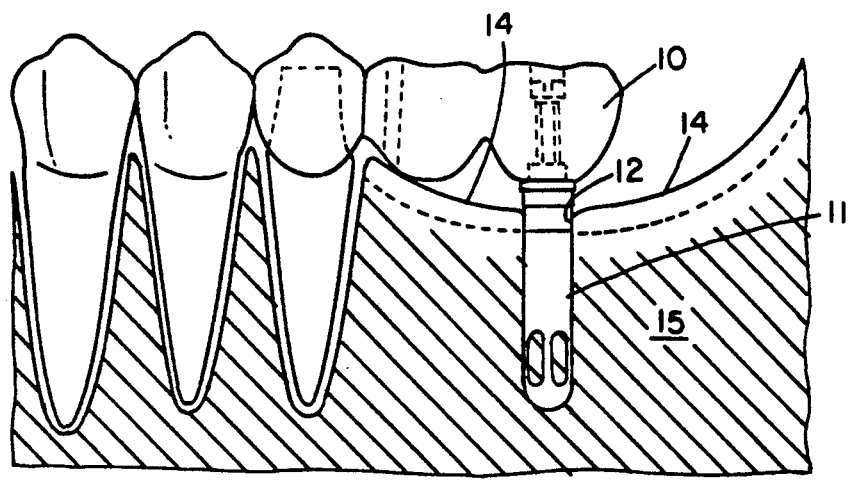
FIGS. 1 A and B illustrate the background in which the invention is used.
Figure 1B:
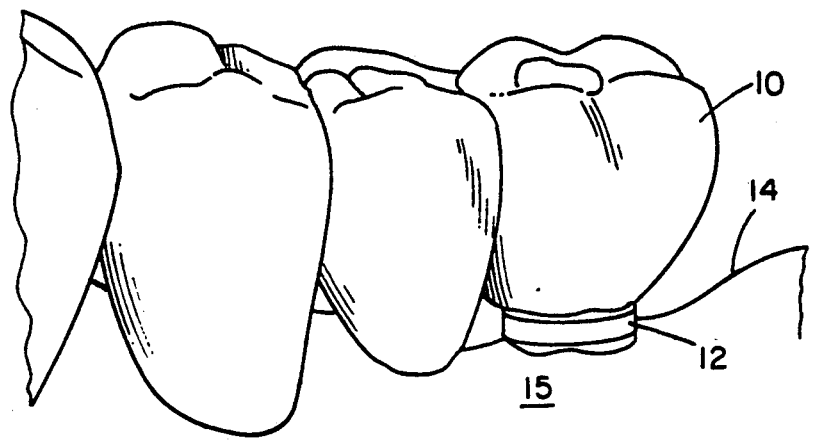

In FIG. 1A a dental reconstruction is shown in which tooth 10 is mounted on a dental implant fixture 11 in jaw bone 15 on which a transmucosal component 12 penetrating the gum 14 supports the tooth. According to the current practice the outer surfaces of the transmucosal component 12 are smooth, in order to prevent the formation of plaque on them. This is similar to the smooth surfaces of natural teeth, some of which are shown in FIGS. 1A and B. FIG. 1B shows the transmucosal component 12 exiting the gum 14. According to current dental practice, dental implant fixtures and the transmucosal components which are affixed to them are made of titanium and dilute titanium alloys as presently preferred materials. Titanium and its alloys are soft compared to the curettes that are normally used in dental hygiene for the purpose of cleaning away plaque, calculus and food debris from teeth at under and above the gum line.

Figure 2:
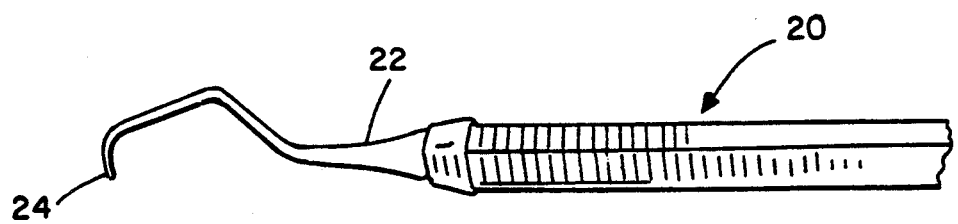
FIG. 2 shows a representative curette to which the invention is applied.

In FIG. 2 a dental curette 20 has an extending arm 22 bent, in this illustrated embodiment, in the shape of a Gracey curve having at its extreme end a tip 24 which is used for dental scaling. It is understood that the invention is not limited to any particular shape of dental scaling tool. The tip 24 is the part of the tool which is applied to teeth at and under the gum line for the purpose of removing or scraping away scale and dental plaque.

FIG. 3B is an enlarged 45° oblique view of the tip 24. FIG. 3A is a top view, and FIG. 3C is a side view of FIG. 3B. FIGS. 3A, B and C, and FIG. 4A show one example of this embodiment of the invention as it may be used in practice. A core 32 is covered with a contact layer 34 made of a material that is softer than titanium. Between the core 32 and the outer layer 34, an intermediate layer 36 is provided which can function as a telltale when the outer layer 34 is worn away. FIGS. 3A, B and C are a generic illustration of a preferred embodiment of the invention. The best mode now known to practice this embodiment is to make the core 32 of brass, copper, or titanium, the outer layer 34 of pure or nearly pure gold, (24K or 23K) and the intermediate layer 36 palladium or nickel. In a practical embodiment of the invention the core is brass, the intermediate layer is palladium from about 0.000010 to 0.000050 micro inch thick, and the outer layer 34 is made of gold at a total thickness of about 0.000150 micro inch. In a more complex example (not illustrated), the core 32 is first covered with a copper flash ranging in thickness from about 0.000010 to 0.000050 micro-inch, and then with a palladium flash having the same range of thickness and then with a thin layer of relatively hard gold strike about 0.000060 micro-inch thick, with the outer contact coat layer 34 of softer gold about 0.000090 micro-inch thick. The palladium flash functions as the intermediate layer 36 in FIG. 3. In each of these described examples, when the layer or layers of gold wears or wear away, the palladium layer becomes apparent to the eye to give warning, and the dentist may then choose to discard the scaling instrument and replace it with a new one. In the second example described, the copper and palladium layers are barriers used to improve the adhesion of the gold to the brass. Other examples of this embodiment of the invention may be made. For example, nickel or silver may be substituted for palladium as the intermediate layer 36 that becomes visible when the gold outer layer or layers is or are worn away. However, silver bleeds into gold over time, so that if the intermediate layer 36 is to be relied upon as a tell-tale, palladium or nickel is preferred.

The intermediate layer 36, alone or with additional layers as described above in some examples, has more than one use. As described above, it is on the one hand a barrier layer used to provide adhesion of the gold layer 34 to the brass core 32. Additionally, if appropriately colored, it may provide a tell-tale indicating when the contact layer 34 of gold and the harder underlying layer of gold if used, has been worn away. The option of a telltale is up to the user and, if not desired, the intermediate layer 36 can be made of a material which does not have a contrasting color with the materials of the outer layer 34.

The outer contact layer 34 may be made of any material that is softer than titanium or its dilute alloy. At the present time titanium and one dilute alloy, TIV6AL4, are in use for implant fixtures and transmucosal abutments mounted on them. The Vickers Hardness (dph) of commercially pure titanium is in the range from 105 to 290; of the alloy from 327-371. Titanium dental abutments are commonly made in one of two grades of commercially pure titanium; one grade has "dph" of 209, the other has "dph" of 235. "dph" for pure gold is about 25-70. "dph" for platinum is about 40-110. "dph" for palladium is about 40-125. Any material that is softer preferably than the lower of these numbers for titanium, whether a metal or an engineering plastics material, or the like, may be used in place of the gold that is illustrated and described in the presently preferred examples of this embodiment of the invention. "dph" for brass ranges from 77 to 220; however brass is not suitable as a contact material because it corrodes.

The core 32 need not be limited to brass, but can be made of any other metal, a plastics material, a reinforced plastic material, a composite material or any other material which can be made into the proper shape with the required strength and resilience. There are several other materials which might have the correct mechanical properties to be used as a core, with the limiting factor usually being the ability to coat such materials with a second material which is softer than and not abrasive to titanium and its dilute alloys, and which is otherwise suitable as the contact material. We have had experimental success using teflon and other plastic coatings on a dental scaler to remove plaque and scale from titanium abutments, the limiting factor encountered up to this time being the inability to develop such a coating that remains on the core for a sufficient length of time, when is made thin enough for proper application, to be practically-useful to the dentist at chairside.

Referring now to FIGS. 3A, B and C, together with FIGS. 4, 5 and 6, an additional embodiment of the invention will be described. The tip 24 has an inner surface 38 which is flat in cross-section and curves along the longitudinal axis (not shown) of the tip. This gives the core 32 a "D" shape, shown reversed in FIG. 4A, which shows the cross-sectional shape used in the prior art. FIG. 4B shows a new feature of the present invention. In the prior art, as represented in FIG. 4A, the flat surface 38 meets the round outer surface 39 of the tip 24 at a sharp edge 40, which is the contacting or scraping edge of the scaler. This sharp scraping edge is a source of the problems to which the present invention is addressed. Any contact material 34, no matter how soft, may have the ability to scratch titanium and its dilute alloys when it is formed with a scaling edge-that is, in effect, a sharp cutting edge. The use of a soft material to perform dental scaling as heretofore described in this specification effectively minimized this risk. According to the presently described embodiment of the invention the contacting edge can be rounded, as is shown at 40' in FIG. 4B, to prevent the scaling tool from scratching titanium and its dilute alloys even if the contacting material is as hard as, or somewhat harder than, titanium and its dilute alloys. A range of radii on which the contacting edge of the scaling surface can be curved has been found which range substantially defines limits of preferred curvatures for the contacting edge 40'. This range of radii is disclosed with reference to FIGS. 5 and 6.

FIG. 5 is a further enlarged view of FIG. 3A on which a series of cross-section marks labeled from A to Z, inclusive, are super-posed on the scaling tip 24. FIG. 6 shows the cross-sections of the tip 24 at those of these cross-section marks the labels of which are encircled in FIG. 5. The cross-section marks in FIG. 5 are spaced apart 10/1000 inch. The rounded contacting edge 40' is marked on each cross-section shown in FIG. 6, together with the radius of curvature of the contacting edge at the cross-section. The radius of curvature of the contacting edge portion of the scaler should be no less than about 0.003 inch and no greater than about 0.012 inch. The optimum range of radii of curvature is from about 0.003 inch to about 0.007 inch. If the radius of curvature approaches zero the sharp contacting edge 40 that is characteristic of the prior art evolves, as appears in FIG. 6, at cross-sections V and X, which are far removed from the tip end of the scaling tip 24, and are not functioning parts of the scaler.

Figure 6:
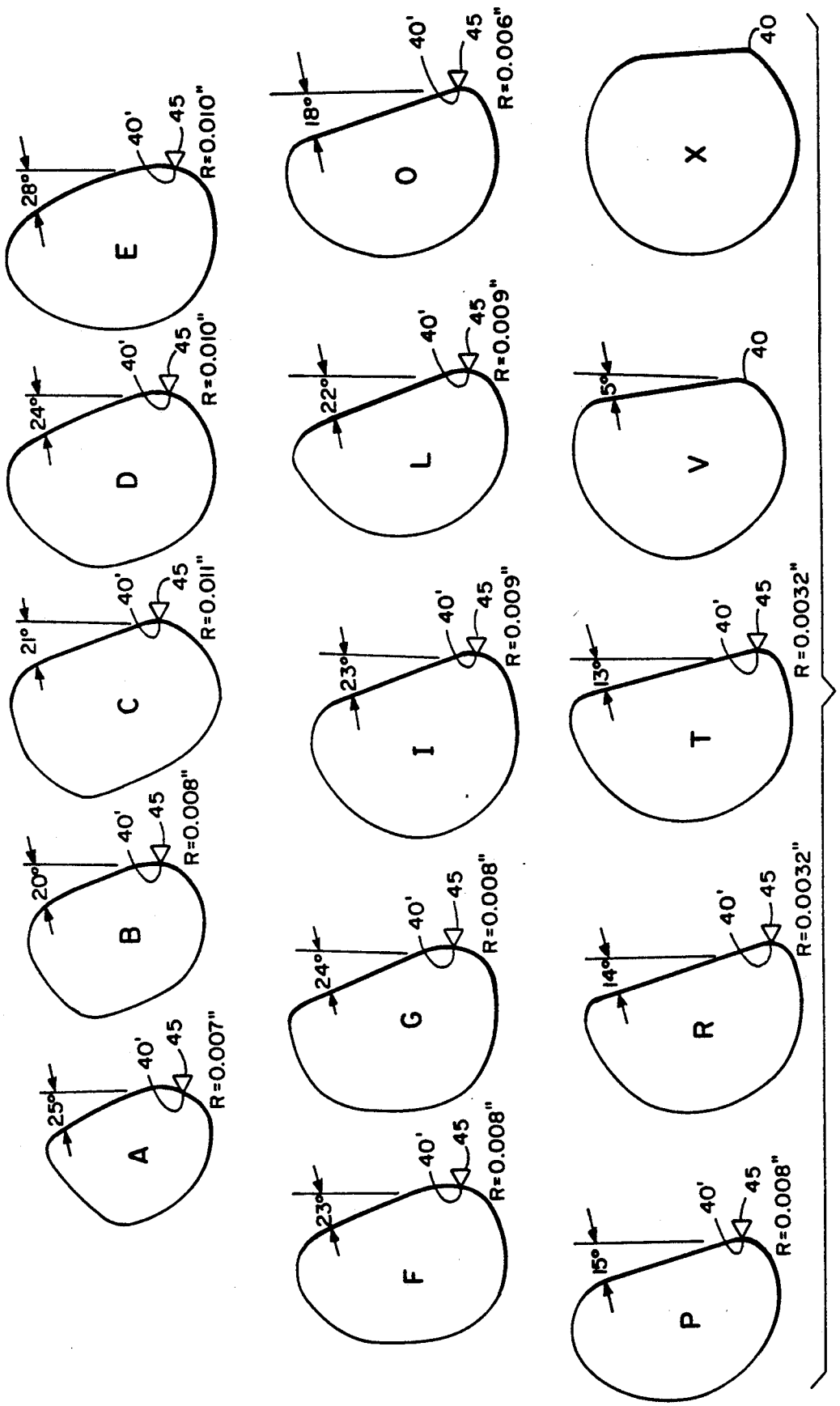
FIG. 6 is a series of cross-sections taken on some of the lines in FIG. 5.

In FIG. 6 the triangular-shaped figure 45 with its apex pointed to the scaling edge 40' denotes the rounded scaling edge. The radius of curvature R is indicated at the apex of the figure 45.

We claim:

1. A dental scaler for use to remove plaque from abutments made of a material having Vickers Hardness in the range of about 105 to 371, said scaler having a scaling tip comprising a support core made of a first material and covering at least a portion of said core a contact layer made of another material that is softer than said abutment material for making contact with said abutment material during use of said scaler, whereby during use of said scaler for removing plaque from such abutments said contact layer will be worn away in preference to scratching said abutment material.

2. A dental scaler according to claim 1 in which the Vickers Hardness of said material of said contact layer is no greater than approximately 100.

3. A dental scaler according to claim 1 in which said contact layer is made of a metal selected from gold, platinum, and palladium.

4. A dental scaler according to claim 3 in which the thickness of said contact layer is about 0.000150 micro-inch.

5. A dental scaler according to claim 4 in which at least the major portion of said contact layer is 24 karat gold substantially 99.99% pure.

6. A dental scaler according to claim 3 in which said contact layer is 24 karat gold substantially 99.99% pure.

7. A dental scaler according to claim 1 in which said support core is made of a first material selected from metals and plastics having strength and resilience properties suitable for scaling dental abutments.

8. A dental scaler according to claim 7 in which said contact layer is made of a metal selected from gold, platinum and palladium.

9. A dental scaler according to claim 8 in which the thickness said contact layer is about 0.000150 micro-inch.

10. A dental scaler according to claim 1 in which a tell-tale layer is provided between said core and said contact layer, for giving a visible indication of the wearing away of said contact layer.

11. A dental scaler according to claim 10 in which said tell-tale layer is made of a metal selected from, palladium, nickel and silver.

12. A dental scaler according to claim 11 in which the thickness of said contact layer is about 0.000150 micro-inch and the thickness of said tell-tale layer is in the range from about 0.000010 to about 0.000050 micro-inch.

13. A dental scaler according to claim 11 in which said contact layer is made of substantially pure gold, including a relatively thin layer of a harder gold between said tell-tale layer and said contact layer.

14. A dental scaler according to claim 13 in which said relatively thin layer of gold is substantially 0.000060 micro-inch thick, and said contact layer of gold is substantially 0.000090 micro-thick.

15. A dental scaler according to claim 13 including a flash layer of copper between said core and said tell-tale layer.

16. A dental scaler according to claim 15 in which the total thickness of said gold layers is about 0.000150 micro-inch, said telltale layer is substantially from about 0.000010 to about 0.000050 micro-inch thick, and said copper flash is substantially from about 0.000010 to about 0.000050 micro-inch thick.

17. A dental scaler according to claim 1 in which said contact layer is made of a plastic material.

18. A dental scaler according to claim 1 having along its scaling tip a scaling contact edge that is rounded in cross-section on a radius not less than about 0.003 inch.

19. A dental scaler according to claim 18 in which said radius is not greater than about 0.012 inch.

20. A dental scaler according to claim 18 in which said radius is not greater than about 0.007 inch.

21. A dental scaler according to claim 20 in which at least the portion of said tip which provides said contact edge is made of a material that is softer than titanium.

22. A dental scaler according to claim 18 in which said contact edge is covered with a contact layer made of a material that is softer than titanium.

23. A dental scaler for use to remove plaque from abutments made of a metal selected from titanium and titanium alloys, said scaler having a scaling tip comprised of a brass support core, a copper flash about 0.000010 to 0.000050 micro-inch thick over said core, a palladium flash of substantially similar thickness over said copper flash, a gold strike layer about 0.000060 micro-inch thick over said palladium flash, and an outer layer of gold about 0.000090 micro-inch thick over said gold strike layer.

24. A dental scaler according to claim 23 in which said outer layer is made of gold that is substantially 99.999% pure.

25. A dental scaler according to claim 24 in which said strike layer is made of gold that is harder than said outer layer.

26. A dental curette for scaling the surface of an artificial article such as a tooth, abutment or the like permanently installed in a human mouth comprising a scaling tip with a scaling contact edge made of a hard material that is not substantially harder than the material having said surface, wherein said contact edge is rounded in cross section on a radius not less than about 0.003 inch for minimizing scratching of said article during scaling thereof.

27. A dental curette according to claim 26 in which the Vickers Hardness of the material of which said contact edge is made is no greater than about 200.

28. A dental scaler according to claim 26 in which said scaling tip comprises a support core and covering at least a portion of said core a layer of said material of which said contact edge is made.

29. A dental scaler according to claim 28 in which said core is made of a material selected from metals and plastics.

30. A dental scaler according to claim 28 in which said contact edge is made of a material that is softer than titanium.

31. A dental scaler according to claim 30 in which said material is selected from metals and plastics.

32. A dental curette according to claim 26 in which said radius is not greater than about 0.012 inch.

33. A dental curette according to claim 26 in which said radius is not greater than about 0.007 inch.

34. A dental curette according to claim 26 in which said contact edge is covered with a layer of a material that is softer than said material having said surface.

35. A dental scaler according to claim 26 in which said contact edge is made of a material that is softer than titanium.

36. A dental scaler according to claim 35 in which said material is selected from metals and plastics.

37. A dental scaler for scaling the surface of an artificial article such as a tooth, abutment or the like permanently installed in a human mouth comprising a scaling tip with a scaling contact edge made of a material selected from the group consisting of gold and alloys of gold, platinum and palladium.

38. A dental scaler according to claim 37 in which said material is 24 karat gold substantially 99.99% pure.

39. A dental scaler according to claim 37 in which said scaling tip comprises a support core and a layer of said material covers at least a portion of said core.

40. A dental scaler according to claim 39 in which said layer is substantially form 0.000090 to 0.000150 micro-inch thick.

41. A dental scaler according to claim 39 in which said layer is made of 24 karat gold substantially 99.99% pure.

42. A dental scaler according to claim 39 in which a tell-tale layer is provided between said core and said layer of said material of which said contact edge is made.

43. A dental scaler according to claim 42 in which said telltale layer is made of a metal selected from palladium, nickel and silver.

44. A dental scaler according to claim 42 in which said contact edge is made of gold.

45. A dental scaler according to claim 44 including a strike layer of gold between said tell-tale layer and said layer of gold of which said contact edge is made.

46. A dental scaler according to claim 45 in which said strike layer is harder than said contact edge layer.

47. A dental scaler according to claim 46 in which said strike layer is about 0.000060 micro-inch thick, and said contact edge layer is about 0.000090 micro-inch thick.

* * * * *